United States Patent [19]
Mileaf et al.

[11] Patent Number: 5,652,149
[45] Date of Patent: Jul. 29, 1997

[54] MIXING APPARATUS & METHOD FOR AN OPTICAL AGGLUTINATION ASSAY DEVICE

[75] Inventors: Daryl S. Mileaf, Jessup; Noe E. Rodgriguez, II, Severna Park, both of Md.

[73] Assignee: Westinghouse Electric Corporation, Pittsburgh, Pa.

[21] Appl. No.: 398,846

[22] Filed: Mar. 6, 1995

Related U.S. Application Data

[63] Continuation-in-part of Ser. No. 986,816, Dec. 8, 1992, Pat. No. 5,500,187.
[51] Int. Cl.[6] .................. G01N 33/543; G01N 33/546; G01N 33/558
[52] U.S. Cl. .................. 436/518; 422/55; 422/57; 422/58; 422/68.1; 422/73; 422/82.05; 435/207.1; 435/207.2; 435/207.3; 435/288.4; 435/288.7; 435/808; 435/810; 435/970; 435/973; 436/165; 436/514; 436/523; 436/531; 436/533; 436/534; 436/535; 436/809
[58] Field of Search .................. 422/55, 57, 58, 422/68.1, 73, 82.05; 435/287.1, 287.2, 287.3, 288.4, 288.7, 808, 810, 970, 973; 436/514, 518, 523, 531, 533, 534, 535, 165, 805, 809

[56] References Cited

U.S. PATENT DOCUMENTS

| | | | |
|---|---|---|---|
| 4,918,025 | 4/1990 | Grenner | 436/165 |
| 5,154,888 | 10/1992 | Zander et al. | 422/58 |
| 5,254,479 | 10/1993 | Chemelli | 436/180 |

*Primary Examiner*—Christopher L. Chin

[57] ABSTRACT

An assay device for detecting the presence of analytes in an unknown sample includes a reaction system wherein resilient storage reservoirs containing reagents are fluidly connected to a track containing the sample. An actuation mechanism forces the reagent from each of the reservoirs into the track where the reagents mix together and with the sample. The mechanism produces a first flow rate and the mechanism is operable to reverse the pressure applied to the reservoirs to reverse the direction of flow of the fluids in the track for a predetermined period of time after which the flow is again reversed. The mechanism then reduces the force applied to allow a second flow rate less than the first flow rate so that reaction can occur whereby a determination may be made as to whether the target analyte is present in the sample.

6 Claims, 10 Drawing Sheets

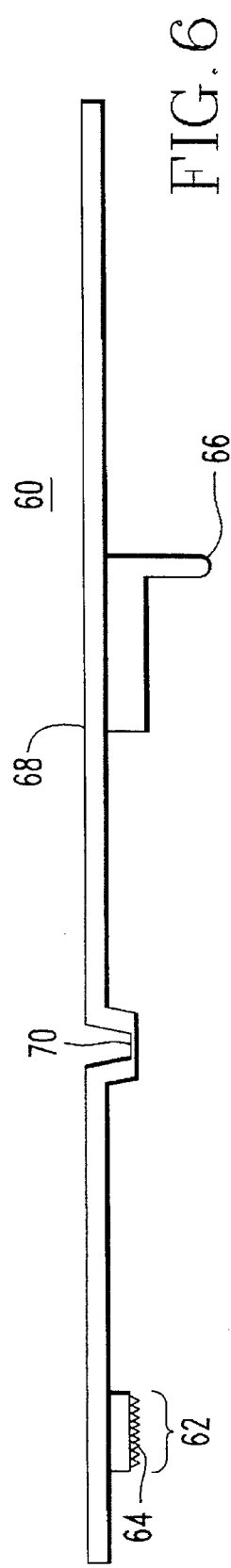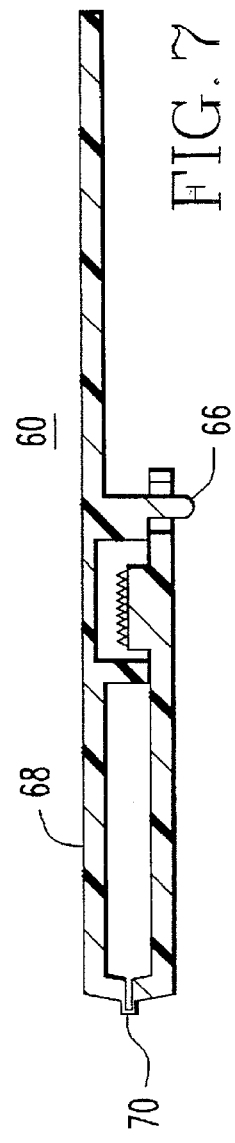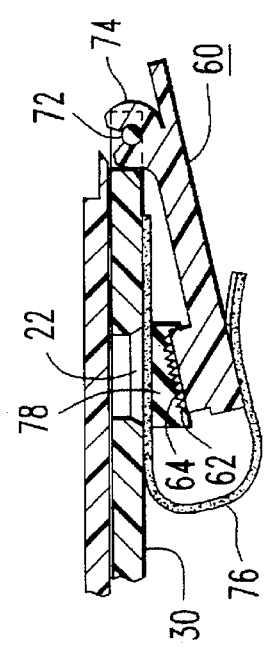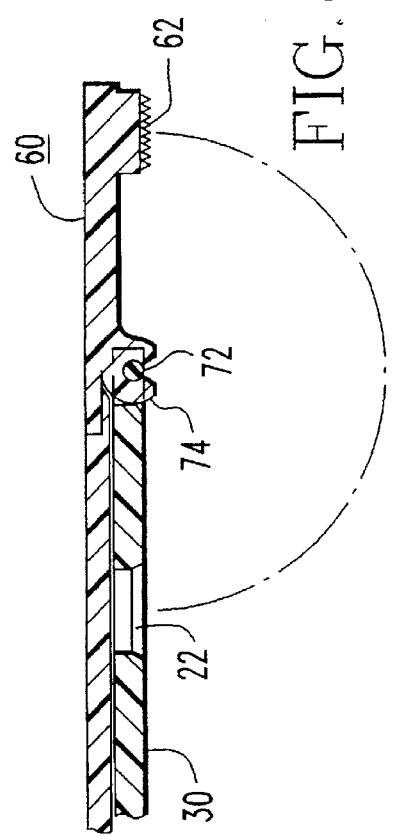

MIXING APPARATUS & METHOD FOR AN OPTICAL AGGLUTINATION ASSAY DEVICE

CROSS REFERENCE TO RELATED APPLICATIONS

This application is a continuation-in-part of application Ser. No. 986,816, filed Dec. 8, 1992, now U.S. Pat. No. 5,500,187.

BACKGROUND OF THE INVENTION

1. Field of the Invention

The present invention relates to devices for detecting the presence of analytes. In particular, the invention relates to such devices whereby disposable assays may be quickly and efficiently conducted in the field. More particularly, the invention relates to an improved arrangement for mixing reagents used in such devices.

2. The Prior Art

There is a present and continuing need to detect a wide variety of analytes with high specificity and high sensitivity in many applications. A technique that is well known in the art uses antibody/antigen (antibody generator) reactions to determine a target analyte. One common use of the antibody/antigen pair is in the construction of a reaction environment in which microscopic particles to which antibody or antigens have been chemically attached are made to agglutinate or are inhibited from agglutinating in the presence of the mating antibody/antigen and the target analyte.

When an agglutination reaction occurs, the microscopic particles chemically bind to each other with the antibody/antigen molecules serving as very specific chemical binding agents, forming much larger aggregates of particles which can grow in size to become visible to the naked eye. The progress of the reaction may be monitored and resulting data analyzed to provide quantitative and qualitative results on target analyte concentration.

A specific agglutination reaction is latex agglutination. Latex agglutination tests are available which detect small qualities of antigen molecules. Agglutination reactions usually involve the aggregation of latex particles which bear on the surface antigenic molecules. Aggregation (agglutination) occurs when antibody molecules specifically corresponding to the antigen (e.g. cocaine) are introduced into the solution of the carrier particles. Antibodies can be visualized as having a "Y" shape where both arms of the "Y" can attach antigen. Mixing antigen-coated latex particles and antibody causes these components to interact and combine. As more antibodies and particles become involved, many cross-linkages are formed and the particles group together as visible clusters. However, when free, unbounded antigen is introduced from an external sample, for instance, agglutination does not occur. The free antigen caps the antibody binding sites and inhibits the agglutination.

Devices are known in the art which can detect various analytes. However, these devices require numerous steps that are not conducive to being used in the field environment, with minimal training, in a simple sequence, to provide consistent results. An assay device designed for ease of use by the person performing the test would be desirable.

Devices are known which require a user to add the required reagents and perform a crude stirring or mixing operation which is subject to not being repeatable in the field. Carrying the required reagents, measuring the exact proportions, and mixing the reagents in the assay device are steps which are not conducive to ease of use with minimal training. It would be desirable to have an assay device which contained the pre-measured reagents needed to perform a specific test to determine if a suspect substance contained a target analyte. Additionally, it would be desirable to have an assay device which was designed to adequately mix the reagents upon being actuated before being introduced to the sample or suspect substance for further mixing.

Known devices require the assay device to be held still or horizontal while the reagent and sample mixture flow through the assay device to get an agglutination result. Some devices require close tolerances in manufacturing to obtain capillary flow. Other known devices require the white room environment of a laboratory. It would be desirable for operators in the field to have an assay device that could be used by simply placing a sample to be tested into the device with an optimal amount of sample being collected by a swab and triggering an actuator which would quickly and repeatedly carry out the test without room for operator error. It would also be desirable to have a device resistant to an abusive environment of rough handling and jostling around even while the test was being conducted.

This application is related to U.S. Pat. No. 5,290,517 entitled "Optical Agglutination Assay Device", filed Apr. 4, 1990 and assigned to the same assignee as the present application and hereby incorporated by reference. While that patent discloses different design configurations for the assay device, it may be utilized with an optical transmitting and receiving unit for measuring the intensity of light reflected from or transmitted through an optical viewing area in a track as a measure of the occurrence of agglutination in the reaction system.

A simple, inexpensive, portable assay device for detection of an unknown analyte with improved mixing of the requisite reagents used in the device, is disclosed herein.

SUMMARY OF THE INVENTION

Apparatus in accordance with the present invention includes an assay card which has an entry port for receiving a sample to be tested. The card additionally includes a plurality of reservoirs each of which contains a reagent and each being resilient such that it reduces in volume when positive pressure is applied to expel the contents and will return towards its original volume when the applied pressure is reversed. A fluid conveying track connects the reservoir to the entry port and extends downstream thereof at which point there is positioned a viewing area to view and analyze the fluid contents of that portion of the track. An actuator means is provided for applying pressure to the reservoirs to expel the content into the track to mix them together and with the sample in the entry port. A detector means is operable to provide an output signal indicative of the presence of the mixed reagents at the viewing area and a control means is provided and is operable in response to the output signal of the detector to cause the actuator means to reverse the applied pressure, at least once, to thereby reverse the direction of fluid flow in the track and to thereafter again apply positive pressure whereby the reversal of fluid flow further agitates and mixes the reagents and sample.

BRIEF DESCRIPTION OF THE DRAWINGS

FIG. 6 is a side view of a swab with protective closure in an opened position;

FIG. 7 is a cross-sectional side view of the swab shown in FIG. 6 in a closed position;

FIG. 8 is a cross-sectional side view of a hinged swab in the opened position;

FIG. 9 is a cross-sectional side view of the hinged swab shown in FIG. 8 engaged with a swab retainer strip;

DETAILED DESCRIPTION OF THE PREFERRED EMBODIMENT

Figure 1:
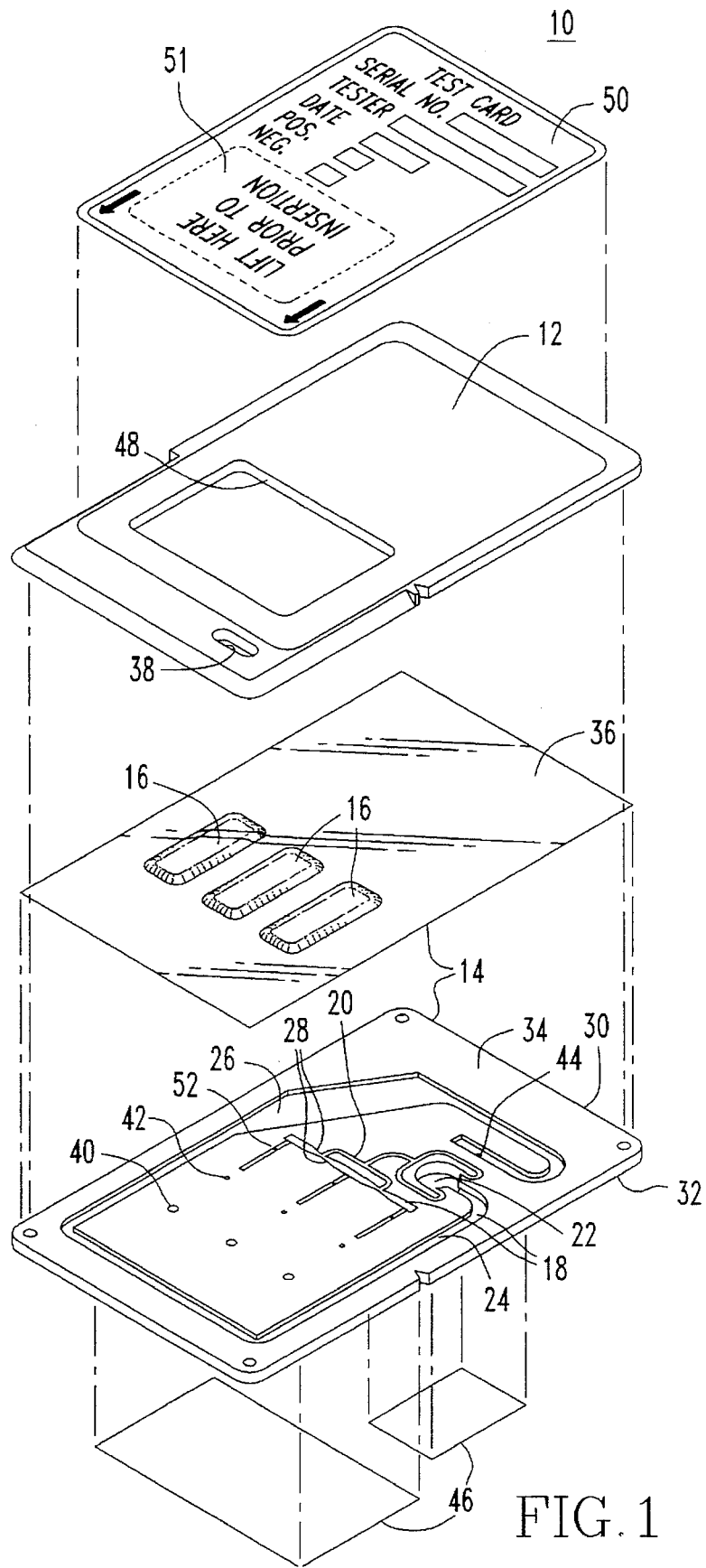
FIG. 1 is an exploded view of an assay device with which the concepts and principles of the present invention may be utilized.
Figure 2:
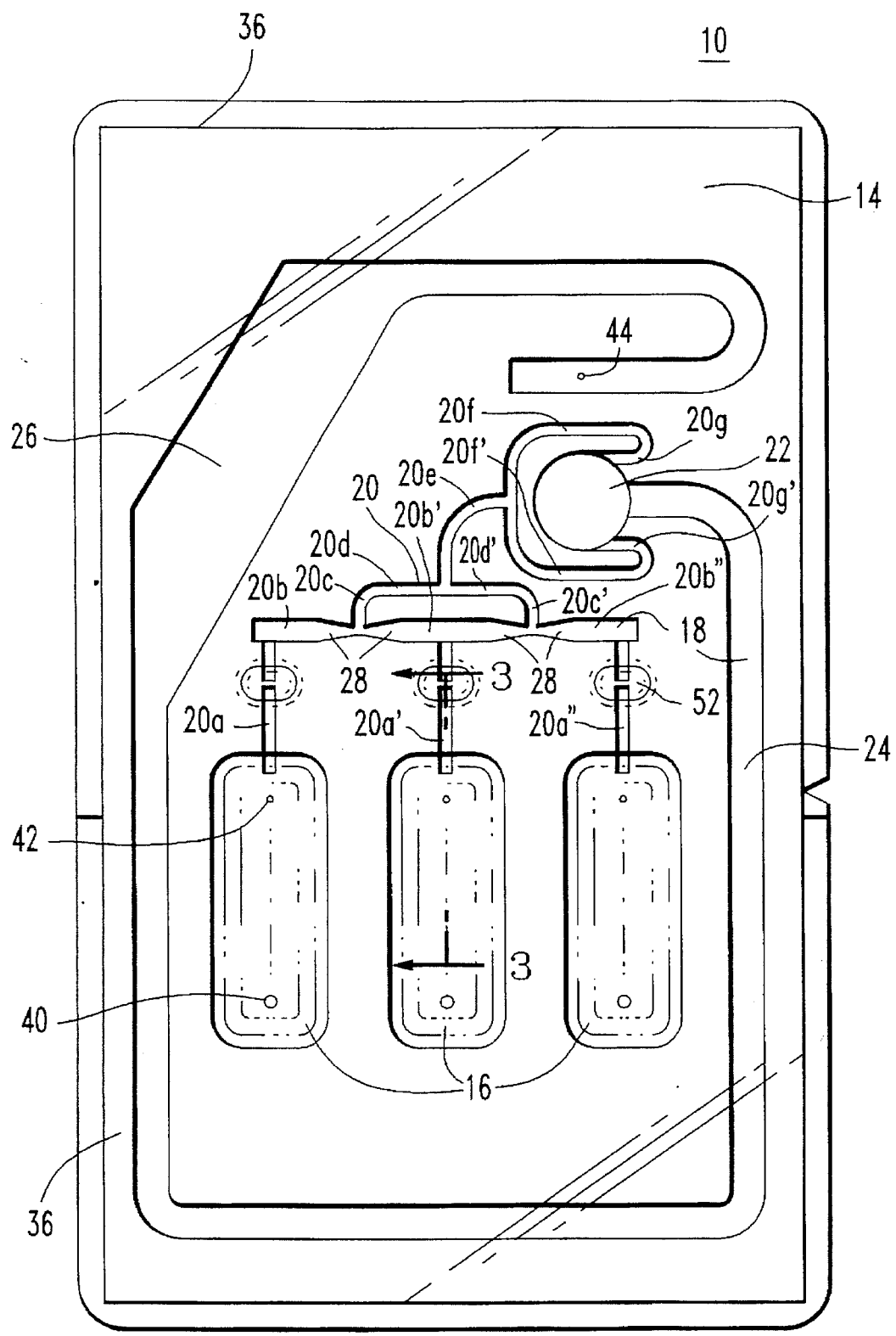
FIG. 2 is a top view of the assay device shown in FIG. 1 without a cover member.

One example of an assay device 10 which may be utilized in conjunction with the present invention is illustrated in FIGS. 1 and 2. FIG. 1 shows an exploded view of the device 10, while a top view of the device 10 without a cover member 12 is illustrated in FIG. 2. Device includes a housing 14, storage reservoirs 16 containing reagent, and track 18. The track 18 which is fluidly connected to the storage reservoirs 16 serves different purposes at various stages of the track 18. The track 18 can be viewed as having the following portions: controlling track 20 fluidly connected to the storage reservoirs 16 for controlling the reagent flow rate and mixing characteristics; receiving track or an entry port 22 fluidly connected to the controlling track 20 for receiving a sample suspected of containing a target analyte into the housing 14; reacting track 24 fluidly connected to the entry port 22 for reacting the reagent and sample mixture; and an accumulator track or accumulator reservoir 26 in the reacting track 24 for retaining excess reagent and sample mixture.

The number of storage reservoirs 16 is dependent upon the reagents required for detecting a particular target analyte. At least one storage reservoir 16 is needed to contain a reagent or mixture of reagents. If a particular set of reagents can be premixed instead of being mixed just prior to actuation with the sample then one storage reservoir may be all that is required.

The controlling track 20 may have any number of fluidly connected paths to the reservoir 16 for dividing, agitating and mixing the reagents. By way of example, and as best illustrated in FIG. 2, the controlling track 20 includes a first portion 20a, 20a' and 20a", each of a predetermined cross-sectional area, in fluid communication with a respective one of the reservoirs 16. Each portion 20a, 20a' and 20a" discharges into a respective second portion 20b, 20b' and 20b", each of a cross-sectional area greater than that of the first portion to which it is connected.

A third portion of controlling track 20 is formed by branches 20c and 20c' which then join with respective fourth portions 20d and 20d'. These fourth portions 20d and 20d' both discharge into a fifth portion 20e of controlling track 20. Fluid in fifth portion 20e is divided in sixth portions 20f and 20f' which bend around to form final and seventh portions 20g and 20g' positioned to discharge fluid tangentially into the entry port 22.

Under circumstances where only one storage reservoir 16 is required, the controlling track 20 may still provide a means for mixing the reagent prior to introducing the reagent to the sample, thereby eliminating any need for shaking the reagent prior to actuation. A nozzle or set of nozzles 28 for assisting in mixing the reagents through changing flow rates and turbulently mixing the reagents together are included in portions 20b, 20b' and 20b" of controlling track 20. Additionally, the nozzles 28 can be used to control the flow rate of the reagent to insure that the reagent flow rate is sufficient to mix the reagent and sample together.

The nozzles 28 serve as a means for mixing the reagents by having the reagents collide at an accelerated speed. In a preferred embodiment the nozzles 28 are molded into the portions 20b, 20b' and 20b" of controlling track 20 to form mixing points. Between nozzles 28, the cross-section of the controlling track 20 may be increased in order to increase the hydraulic diameter of the controlling track 20, which in turn lowers the frictional head loss in the controlling track 20. Lower head loss will allow more actuation energy used to force reagent from the reservoirs 16 to be used to increase fluid velocity instead of frictional losses. The nozzles 28 may be created by stepping the controlling track 20 up or down in cross-section. However, the preferred method is ramping the controlling track 20 with smooth, straight or curved tapers. Not only does this method lower the frictional head losses, but results in fewer air bubbles entering the system. A preferred embodiment of controlling track 20 has the reagent flow turn ninety degrees into portions 20c and 20c' after a head-on collision of the reagents. After the reagents collide and are turned to continue further down the controlling track 20, the controlling track 20 is slightly larger in cross-sectional area so that no unnecessary flow resistance is created. The number of nozzles 28 used in a particular assay device 10 may vary with the specific reagent flow rate and mixing characteristic requirements.

Referring once again to FIG. 1, the optical agglutination assay device 10 includes a card 30 having a first surface 32 and an opposing surface 34 with an entry port 22 extending from the first surface 32 to the opposing surface 34. A flexible transparent member 36 contacts the opposing surface 34 of the card 30 forming at least one reservoir 16 containing reagent and covering the track 18, which is molded into the opposing side 34 of the card 30. At least one controlling track 20 for controlling the reagent flow rate and mixing characteristics is defined by the flexible member 36 and the card 30 through which the reagent can be transferred between the reservoir 16 and the entry port 22. The flexible member 36, such as a polyester film, is resilient and deformable to allow the reagent to be forced between the reservoir 16 and the entry port 22. The reacting track 24 is fluidly connected to the entry port 22 for reacting the reagent and sample mixture. The reacting track 24 has an optical viewing area 38 for viewing the results of mixing the reagents and the sample to determine whether or not the target analyte is present.

In a preferred embodiment the flexible member 36 covers the entry port 22 on the opposing surface 34 of the card 30 as well as the track 18 which is preferably recessed into the opposing surface 34 of the card 30. Additionally, in an alternative embodiment the card 30 and flexible member 36 may be composed of a single piece housing 14 having a flexible top surface.

Preferably the card 30 is made of molded plastic, such as polystyrene. The track 18 through which the reagent flows is molded directly into the card 30. The reservoirs 16 are vacuum-formed into the sheet of polyester film, while the film is being heat-sealed over the side of the card 30 in which the track 18 is molded. This straight-forward process takes less than a minute to complete.

Fill holes 40 are used for filling the reagent storage reservoirs 16 with reagent. Vent holes 42 allow excess air to be displaced from the system during the filling process. Another ventilation hole 44 is shown at the opposite end of track 18 from where the track 18 connects to the reservoirs 16. The purpose of this ventilation hole 44 is to permit any excess air to escape from the track 18 when the reagents are forced from the reservoirs 16. Tape 46 covers the holes 40, 42, and 44 respectively. The tape 46 covering ventilation hole 44 is preferably removed prior to conducting a test with the device 10.

To prevent reaction product from leaking out of the ventilation hole 44 the accumulator reservoir 26 is molded into the reacting track 24. This cavity has the capacity to hold all of the reagent volume in the reservoirs 16.

In a preferred embodiment a cover member 12 made of molded plastic is used to sandwich the flexible member 36 between the card 30 and the cover member 12 to protect the system from being ruptured. Additionally, the cover member 12 has an opening 48 to allow access to the reservoirs 16 for actuating the device 10 by applying pressure to the reservoirs 16 to force the reagents through the track 18. The reservoirs 16, which are not as high as the cover member 12 is thick, protrudes into the opening 48. The optical viewing area 38 is in the cover member 12 to enable the reaction of the reagents and sample or reaction product as it passes through the reacting track 24 to be observed to determine the results of the test. The cover member 12 is ultrasonically welded to the card 30; although the cover member 12 could also be attached with adhesive or doubled-sided tape, by way of example.

A removable label 50 may be provided to cover opening 48 in the cover member 12 to further protect the reservoirs 16 from accidental actuation. Additionally, the label 50 provides information identifying the target analyte the device 10 is designed for testing. A portion 51 of the label 50 covering the reservoirs 16 and viewing area 38 is simply removed after the sample has been introduced to the device 10 and the user desires to carry out the test. The label 50 is made of stiff paper and coated with a high tack/low tack adhesive so that it can be easily and cleanly removed by the user at the appropriate time.

Figure 3:
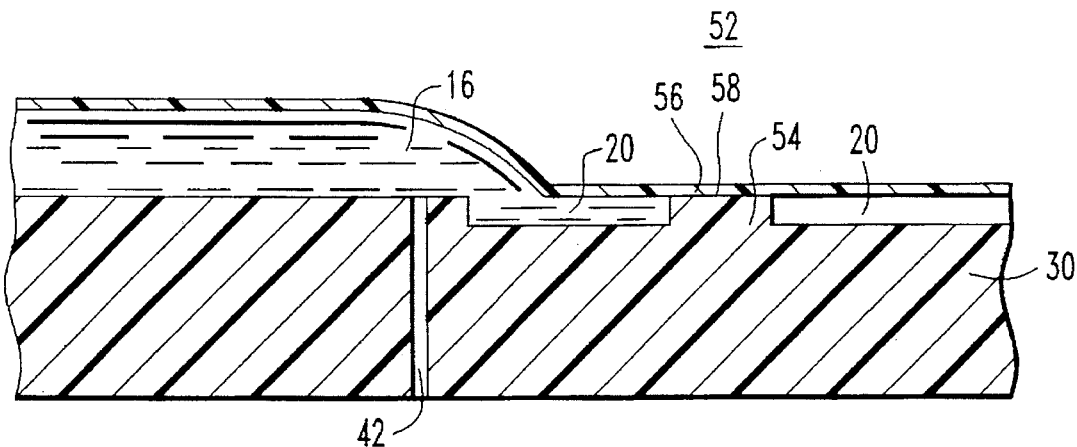
FIG. 3 is a cross-sectional view taken essentially along the line 3—3 of FIG. 2 showing a storage reservoir, controlling track, barrier and yielding member prior to actuation.
Figure 4:
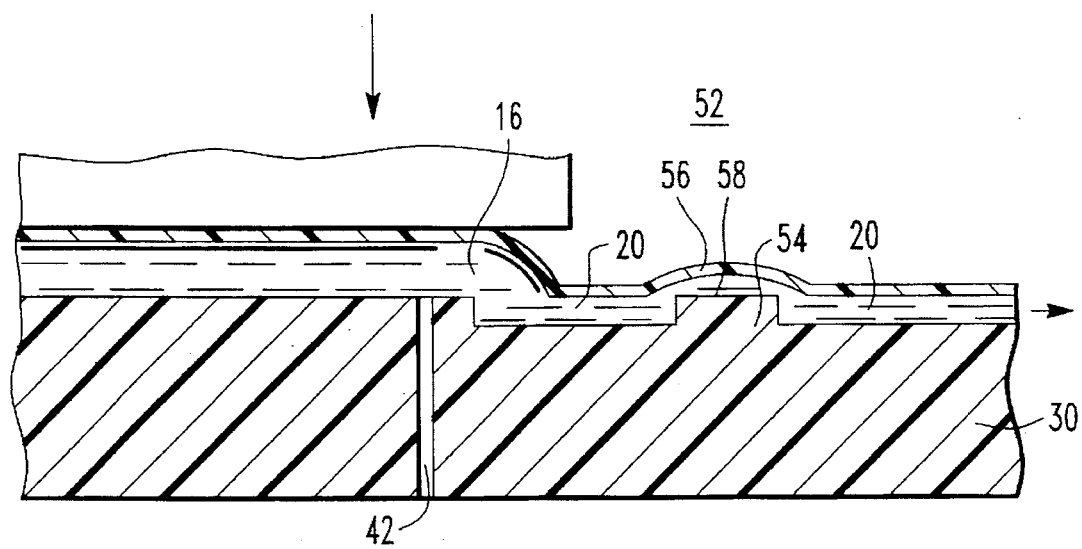
FIG. 4 is a view as in FIG. 3 illustrating a storage reservoir, controlling track, barrier and yielding member during actuation.

A means 52 for preventing the reagents from leaking from the reservoirs 16 due to jarring or dropping the device 10 is shown in FIGS. 1 and 2 and illustrated in cross-sectional view FIGS. 3 and 4. The preferred means 52 for preventing reagent leaking until actuated by an operator utilizes a controlling track barrier 54 and a yielding member 56.

The barrier 54 is molded directly into the card 30 as shown in FIGS. 1–4. The barrier 54 is essentially a break in the controlling track 20 leading out of each reservoir 16. The top 58 of the barrier 54 is coplanar with the opposing surface 34 of the card 30. The wall of the barrier 54 closest to the reagents is preferably perpendicular to the bottom of the track 18 or has a reverse slope so that the fluid is not directed up over the barrier 54. A platen, which is used to seal the polyester film to the card 30, contains a cavity directly above the barrier 54. The cavity covers a larger area than the top 58 of the barrier 54. This cavity is vented to the ambient atmosphere, so that the heated air in the cavity can escape during sealing. If the cavity were not vented, the air within the cavity would increase in pressure, thereby causing the film to seal to the top 58 of the barrier 54. When the heat sealing operation is completed, the heat seal film ends up lying against the top 58 of the barrier 54, thus closing off the passage to the controlling track 20. This prevents the reagents from moving down the track 18 if the card 30 is jarred, shaken or dropped. However, when pressure is applied to the reagents contained in the reservoirs 16, such as occurs during actuation, the reagents will flow through the track 18 and over the top 58 of the barrier 54 by deflecting the yielding member 56, as illustrated in FIGS. 3 and 4.

The introduction of the barrier 54 into the track 18 also creates some resistance to the reagent flow when the reagents are forced out of the reservoirs 16. Some of the energy applied to the reservoirs 16 during actuation is used to push the fluid up and over the barrier 54. A portion of the energy is used to deform the yielding member 56.

The device 10 is intended for use with any reagents capable of utilization in determining the identity of a target analyte where the ease, convenience and reliability of having a self contained system are desired. Specifically, in an agglutination reaction, it is known in the art that a reaction between reagents and a target analyte may be designed to produce agglutination or the inhibition of agglutination. One example may utilize a latex agglutination reaction method for detection where antibodies are able to recognize minute quantities of the substance of interest, for example, cocaine. Latex agglutination reagents which detect various drugs of abuse are commercially available from Roche Diagnostics, Nutley, N.J.

Each of the known test kits is packaged as a set of three reagents for testing for cocaine, one of which is a solution of latex particles. For optimal effectiveness, the latex particle solution must be shaken immediately prior to use. This is recommended because the latex particles have a density greater than the surrounding solution causing the latex to settle over short periods of time.

It is preferred that the reagents used in the assay device 10 eliminate the need for shaking the latex particle solution. The density of the latex particle solution is increased to equal the density of the latex particles thereby preventing particle settling.

Roche Diagnostics provides a latex agglutination test kit for cocaine detection containing: an antibody reagent A—one vial of mouse monoclonal anti-cocaine antibody in a buffered solution; reaction buffer B—one vial of buffer reagent; and latex reagent C—one vial of latex-cocaine particles in a buffered solution.

The Roche Diagnostics test requires the sequential addition of one drop of each reagent with an external or suspect sample. However, the procedure recommends "invert(ing) reagent C approximately 8 to 10 times before use. If excessive foaming is observed allow it to settle before using."

A preferred embodiment of the latex reagent would include the addition of 133 milligrams of sucrose in a final volume of 1 milliliter of latex reagent C creating a latex particle solution having a solution density of 1.05 gram/milliliter, equaling the density of latex particles. As a result, the latex particles remain suspended in the buffered solution and the requirement for inversion of reagent C prior to use is eliminated.

To assess the effectiveness, samples were tested utilizing the reformulated C reagent in the latex agglutination test for cocaine. Ten positive samples (buffer containing 100 parts per million cocaine) and ten negative samples (buffer containing 10 parts per billion cocaine (less than the cut-off value) were tested. Each test produced the appropriate positive or negative result.

This process can be used to enhance the effectiveness of other latex agglutination tests for drug detection. For instance, latex agglutination tests for morphine (heroin), phencyclidine (PCP), marijuana and methamphetamine are commercially available in a similar design as the cocaine test kit discussed above. Respective C reagents from each of these latex agglutination tests can be modified as described above resulting in an easier to use product.

One embodiment of the assay device 10 includes three storage reservoirs 16 for containing the cocaine detecting reagents discussed above, and the nozzles 28 at the head-on collision which are not symmetrical. The nozzle 28 for the center reservoir 16 is only tapered in one dimension, instead of two. The point at which the collision occurs is not on the centerline of the downstream portion (20c or 20c') of the controlling track 20. The intersection is biased towards the center reservoir 16 so that more of the outer reservoir 16 reagent flows through the intersection. This is done because each of the three reservoirs 16 contains the same amount of reagent, but the contents of the center reservoir 16 is divided equally between the two initial collisions, i.e. one collision with the reagents of the other two reservoirs 16.

The shape of the nozzles 28, as well as the location of the collision point, work together to mix equal volumes of the reagent from the center reservoir 16 with the reagents from the remaining two reservoirs 16. The shape and size of the nozzle 28, along with the dimensions of the controlling track 20 preceding the nozzle 28, i.e., the cross-sectional areas of respective portion 20b, 20b' and 20b", can be adjusted based on the properties of the fluids involved and the mixing ratios desired.

Figure 5:
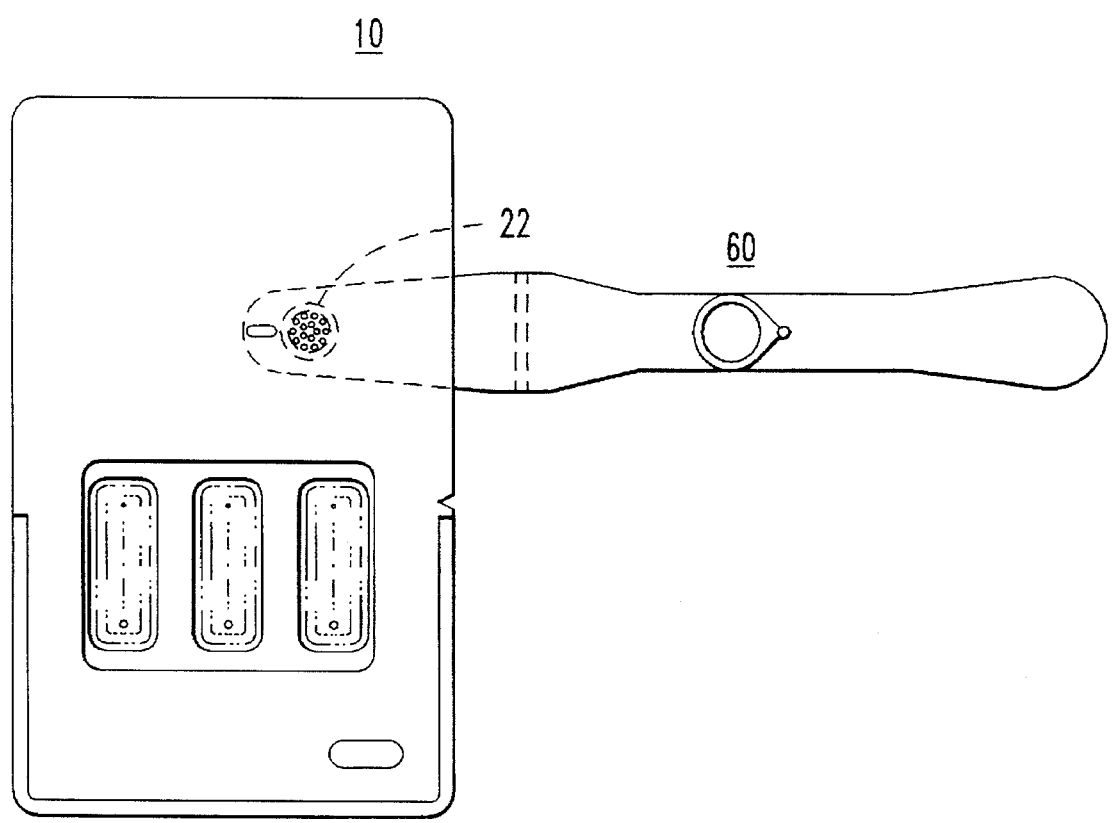
FIG. 5 is a top view of the assay device with an engaged swab.

A delivery means 60 for delivering the sample suspected of containing a target analyte into the device 10 is illustrated in FIG. 5. One type of delivery means 60 for conveying the sample to the assay device 10 is a swab 60. FIG. 5 shows a top view of a preferred assay device 10 with the swab 60 engaged into the entry port 22. Swab 60 is used to collect an unknown sample by rubbing it in the sample or by simply moving it along a surface which is suspected of having been contaminated. The device 10 works by mixing the reagents contained in reservoirs 16 with the sample introduced to the system by the swab 60. After mixing, the results may be determined by analyzing the solution in the reacting track 24.

The cylindrical interface between the preferred swab 60 and the entry port 22 is both easy to manufacture (i.e. mold) and easy to use. A sharp, tapered ridge around the inside of the entry port 22 acts like the barb on a fishhook, allowing the swab 60 to be easily pushed past the ridge in one direction, while preventing it from easily being removed in the opposite direction. The ridge digs into the surface of the swab 60, which is preferably made of a soft plastic, to create a fluid seal.

The swab 60 illustrated in FIG. 6 is in the fully opened position, while FIG. 7 illustrates the closed or protected position. To improve the reliability of mixing the reagents with the sample, the gathering surface 62 of the swab 60 is covered with many closely spaced, small cones 64 which are used to collect the sample particles as the swab 60 is brushed across a surface. The cones 64 are preferably close to one another to grasp and hold the sample particles, while not being unnecessarily tall, minimizing the chance of forming bubbles and limiting the reagents needed to fill the entry port 22. A snap 66 on the swab 60 maintains the closed position until the user unfolds it for use. The design of the swab 60 enables the user to hold and open the swab 60 with one hand. The swab 60 is held in one hand with the middle of the fore finger behind a protective closure 68 and the thumb against a hinge 70 which creates a couple to snap the swab 60 open.

A preferred device 10 will minimize the bubbles created during actuation. Differences in height and the shape of the track 18 at various stages, as well as the cones 64 of the swab 60, tend to create air bubbles in the mixture which increases the difficulty in determining test results. Air bubbles can be a problem if caught in the track 18 under the optical viewing area 38, thus inhibiting the true reagent/analyte reaction from being observed.

A preferred entry port 22 is cylindrical to enhance fluid flow while minimizing bubble formation. The reagents are simultaneously injected, tangentially, into the entry port 22 such that the reagents collide once again before flowing past the cones 64, mixing with the sample particles as the reagents advance toward the reacting track 24. Since the controlling track 20 and the reacting track 24, where they are connected to the entry port 22, are both shallower than the entry port 22 to minimize the amount of required reagents, the track 18 is ramped into and out of the entry port 22. The reagents exit the entry port 22 and enter the reacting track 24 in a direction opposite to that which the reagents are injected into the entry port 22. This results in a more complete filling of the entry port 22 and better flushing of the samples from the collection cones 64.

An alternative embodiment of the swab 60 is illustrated in FIGS. 8 and 9 in the open and sealed position respectively. A hinge pin 72 is molded into the edge of the card 30 enabling the swab 60 to be snapped onto the card 30, thereby creating a device 10 with an attached hinged swab 60. The attached swab 60 incorporates a snap-on hinge 74 for attaching the swab 60 to the pin 72. Additionally, a retainer strip 76 is used to hold the attached swab 60 in a stored position, while keeping the gathering surface 62 clean and sealing the reagents inside the device 10.

The retainer strip 76, shown in FIG. 9, provides a means of sealing the entry port 22, sealing the ventilation hole 44 and protecting the swab gathering surface 62 between manufacture and final use of the device 10. The entry port 22 should be sealed to prevent reagent evaporation and contamination. The cones 64 of the attached swab 60 should be kept free of contamination prior to use. A preferred retainer strip 76 is one piece which performs the desired functions in a simple, easy to use manner. Preferably a narrow, thin strip of polyester film or similar material provides the main structure for the retainer strip 76. Portions of both sides of this strip 76 are adhesive coated so that it will stick to the device 10 and swab 60. It is desirable not to have adhesive over the ventilation hole 44 and entry port 22 since the adhesive may outgas into the track 18 resulting in reagent contamination during storage. A soft rubber pad 78 is laminated to the side of the strip 76 which is opposite the entry port 22 opening. The cones 64 of the gathering surface 62 are pressed into the pad 78 to prevent contamination. The swab 60 is held against the pad 78 by bending the retainer strip 76 over the tip of the swab 60 and adhering it to the back of the swab 60. Additionally, a detent feature in the hinge 74 helps keep the swab 60 against the pad 78.

To use the device, the free-end of the retainer strip 76 will be pulled off of the swab 60. The swab 60 can then be opened to its other detent position. The retainer strip 76 is then peeled off of the device 10, thus opening the entry port 22 and ventilation hole 44. The suspect sample can then be sampled with the swab 60 and then folded into the entry port 22 before actuating the device 10.

Figure 10:
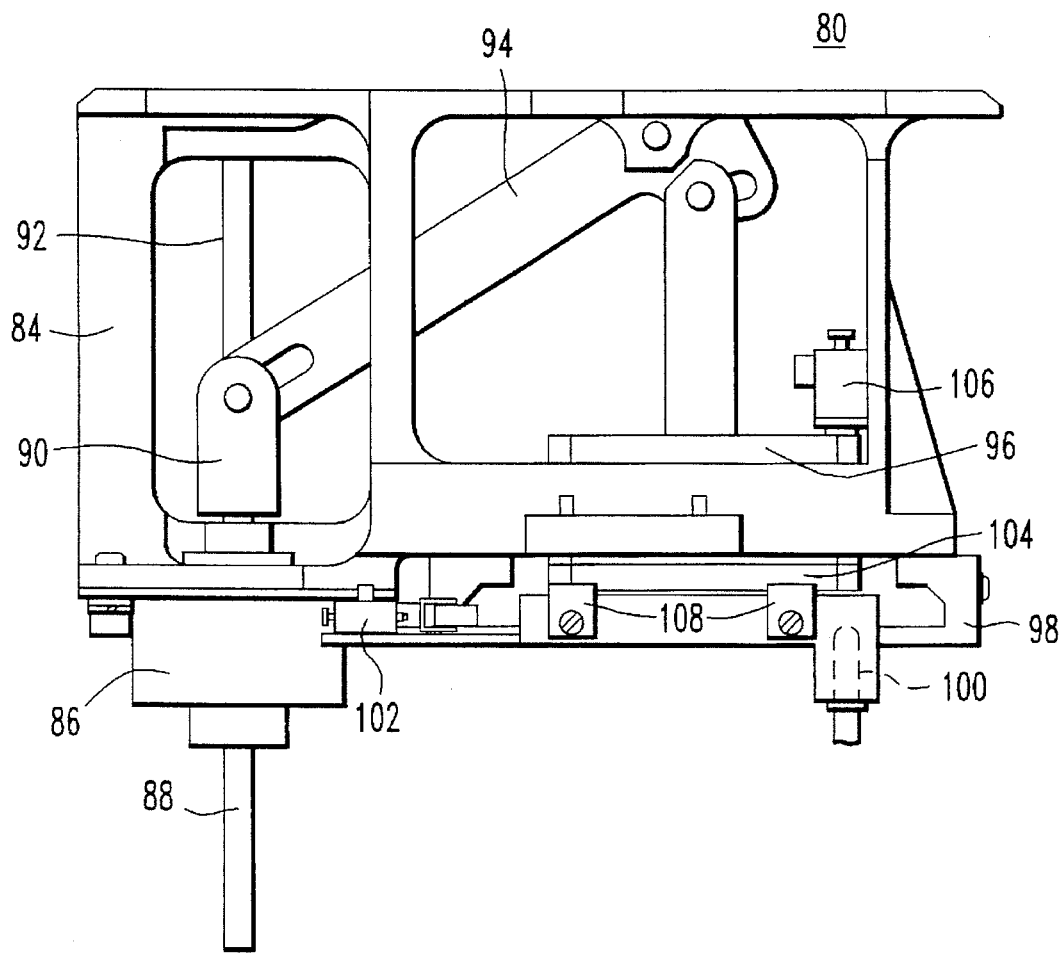
FIG. 10 is a side view of an actuator mechanism.

As illustrated in FIG. 10, a means 80 for actuating is used to macroscopically mix reagents with the sample, then microscopically mix the reagents and sample to allow reaction to occur. The device 10 is preferably utilized in conjunction with a multi-speed actuation mechanism 80 which actuates the device 10 by squeezing the reagents from the reservoirs, mixing the reagents together, and then mixing the reagents with the suspect sample. The reagent and sample mixture may then be analyzed to determine sample identity. To insure that the reagents mix properly with the suspect sample and the proper reaction occurs, the mixing needs to be controlled and predictable. Both macroscopic, large scale mixing of the reagents, and microscopic, molecular diffusion, mixing takes place. The mechanism 80 provides the force and speed profiles to produce the desired mixing conditions.

FIG. 10 shows a side view of the mechanism 80, and the components shown include a mechanism support 84, stepper motor 86, motor shaft 88, drive block 90, motor guide shaft 92, 10:1 mechanical advantage linkage 94, actuation block or platen 96, device or card guide 98, illuminating element such as an LED 100, on/off switch 102, and rubber pad 104. The device guide 98 is a separable subassembly from the actuation mechanism 80. The guide 98 is used to properly position the device 10 in the mechanism 80 by using keying features in the guide 98 and the device 10 to ensure proper device 10 orientation. The guide 98 houses the LED 100 used to illuminate the reaction product through the viewing area 38 and holds the mechanism on/off switch 102.

During operation, the motor shaft 88 moves 0.001 inch per motor pulse. The motor shaft 88 pushes on the drive block 90 which is guided by the motor guide shaft 92. This motion is translated to the linkage 94. The linkage 94 rotates clockwise about its pivot point. This rotary motion is transformed back to linear motion in the platen 96 by a pin in the platen 96 riding in a cam profile slot in the linkage 94. The platen 96 moves down 0.0001 inch when the motor shaft moves up 0.001 inch. The force output by the platen 96 is up to twenty-five (25) pounds which is ten (10) times the maximum motor force output of two and a half (2.5) pounds. The linkage 94 provides a ten (10) to one (1) mechanical advantage to the mechanism 80. The cam profile and straight slots in the linkage 94 maintain this relationship throughout the full range of mechanism 80 travel. The resulting motion of the platen 96 is one tenth (1/10) the motion of the motor shaft 92 with ten (10) times the output force of the motor 86. The amount of force generated by the mechanism 80 depends on the resistance to motion at the platen 96. If the mechanism 80 is operated without inserting a device 10, it will operate with no load. With the device 10 in place, the force transmitted to the platen 96 will equal the resistance from the reagents traveling in the track 18 and the amount of compression of the rubber pad 104 connected to the bottom of the platen 96.

A reset switch 106 is used to turn the motor 86 off when the mechanism 80 direction is reversed. This insures that the mechanism 80 will begin its motion profile from a known or home position. The rubber pad 104 is used to insure smooth actuation of the reservoirs 16. The pad 104 conforms to the reservoirs 16, resulting in equal or near equal actuation of each reservoir 16.

Detent springs 108 are used to hold the device 10 in position during actuation and provide positive device 10 insertion feedback to the user. When the device 10 is fully inserted, it snaps into place due to the force of the springs 108.

Figure 11:
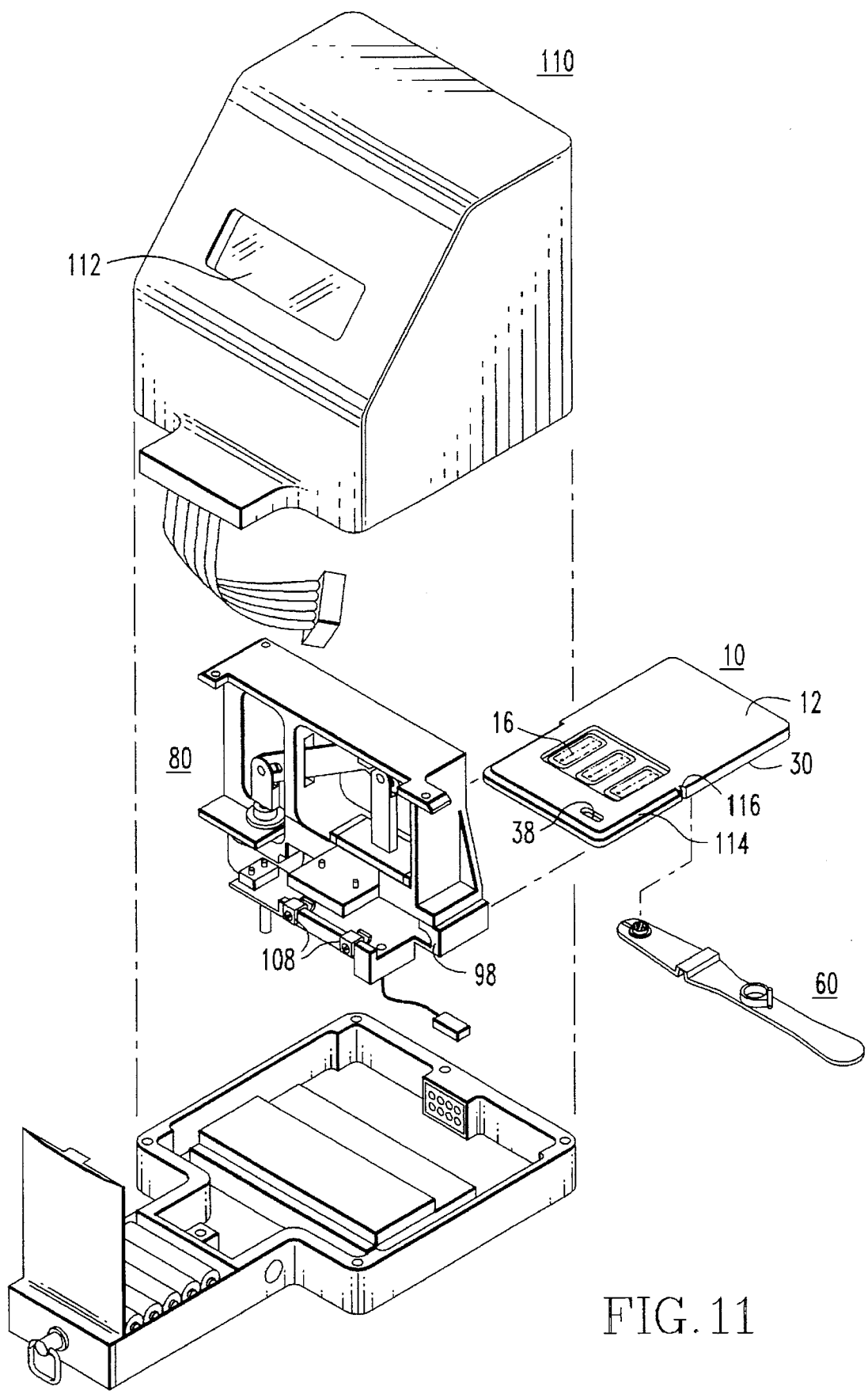
FIG. 11 is an exploded view of the assay device and swab in use with the actuator and electronics which evaluate the test results.

FIG. 11 shows an exploded view of a hand held actuating and reading unit 110 including the actuation mechanism 80. The mechanism 80 provides the interface between the unit 110 and the assay device 10.

Once the sample is in the device 10, the device 10 is partially inserted into the unit 110. This action trips the switch 102 in the unit 110, causing its motor-driven platen 96 to squeeze the reservoirs 16, whereby the reagents flow into the track 18 to mix with each other and then the sample. Photoelectric detectors within an optics assembly view the resulting reaction product and transmit data to a processor. The processor analyzes the data, determines whether the sample does, or does not contain the analyte of interest, and then sends the appropriate message to a display 112.

As shown in FIG. 11, one end of the cover member 12 of the assay device 10 has a chamfer 114 along the top edge and approximately half way up the adjacent sides. This is the end of the device 10 which is inserted into the unit 110. The end chamfer 114 provides a lead-in feature to assist in guiding the device 10 into a slot in the unit 110. The side chamfers 114 match up with corresponding features in the slot and guide 98. This prevents the device 10 from being inserted incorrectly, either upside-down or backwards.

When the device 10 is fully inserted into the unit 110, a V-shaped detent 116 in the edge of the card 30 and cover member 12 assembly accepts a spring-loaded ball when the device 10 is fully inserted. In addition to providing the user with tactile feedback, this detent 116 prevents the device 10 from falling out of the unit 110. When the device 10 is fully inserted into the unit 110, the on/off switch 102 is triggered, turning the unit 110 on. The motor 86 of the mechanism 80 actuates the linkage 94 and platen 96 that press on the reservoirs 16 of the device 10. The reagents are forced out of the reservoirs 16, mixed together in the controlling track 20, mix with the sample in the entry port 22, flow into the reacting track 24 and pass the viewing area 38. The mixing of the reagents which occurs in the controlling track 20 is macroscopic and is done with the mechanism 80 at a first speed creating a first flow rate. When the reagent and sample mixture flows pass the viewing area 38, the mechanism 80 is signaled to switch to a second speed creating a second flow rate less than the first flow rate for continued microscopic mixing of the reaction product.

In a preferred embodiment, the first speed is 200 motor pulses per second, while the second speed is 1 motor pulse every 1.6 seconds. The second speed is continued until the analysis of the reaction product passing the viewing area 38 is complete. Once the analysis is complete, the motor 86 direction is reversed, raising the platen 96 and pad 104 off the reservoirs 16 of the device 10. The unit 110 shuts off when the device 10 is removed.

The actuation mechanism 80 for use with an assay device 10 having a reservoir 16 containing reagent and a track 18 containing a sample connected to the reservoir 16 includes means for providing a first flow rate for mixing and delivering the reagent to the sample; and means for reducing the first flow rate to a second flow rate for further mixing the reagent and sample mixture to provide reaction time. This process can occur by applying pressure to the reservoirs 16 to force the reagent flow or by applying pressure directly to the reagent itself through a piston or plunger type arrangement. Although a preferred driving force is the stepper motor 86, other preferred driving forces are hydraulics, pneumatic or even using the air pressure itself to blow the reagent out of the reservoirs 16.

The actuation mechanism 80 also includes means for programming the means for providing the first flow rate and the means for reducing to the second flow rate according to the properties of the reagents and sample.

In order for the system to function properly, the reagents must be mixed into a homogeneous solution for the desired chemical reaction. With the present invention, the mixing of the reagents and the sample is maximized resulting in a corresponding improvement in system performance, and to this end reference is made to FIGS. 12 through 14 illustrating one embodiment of the present invention.

Figure 12:
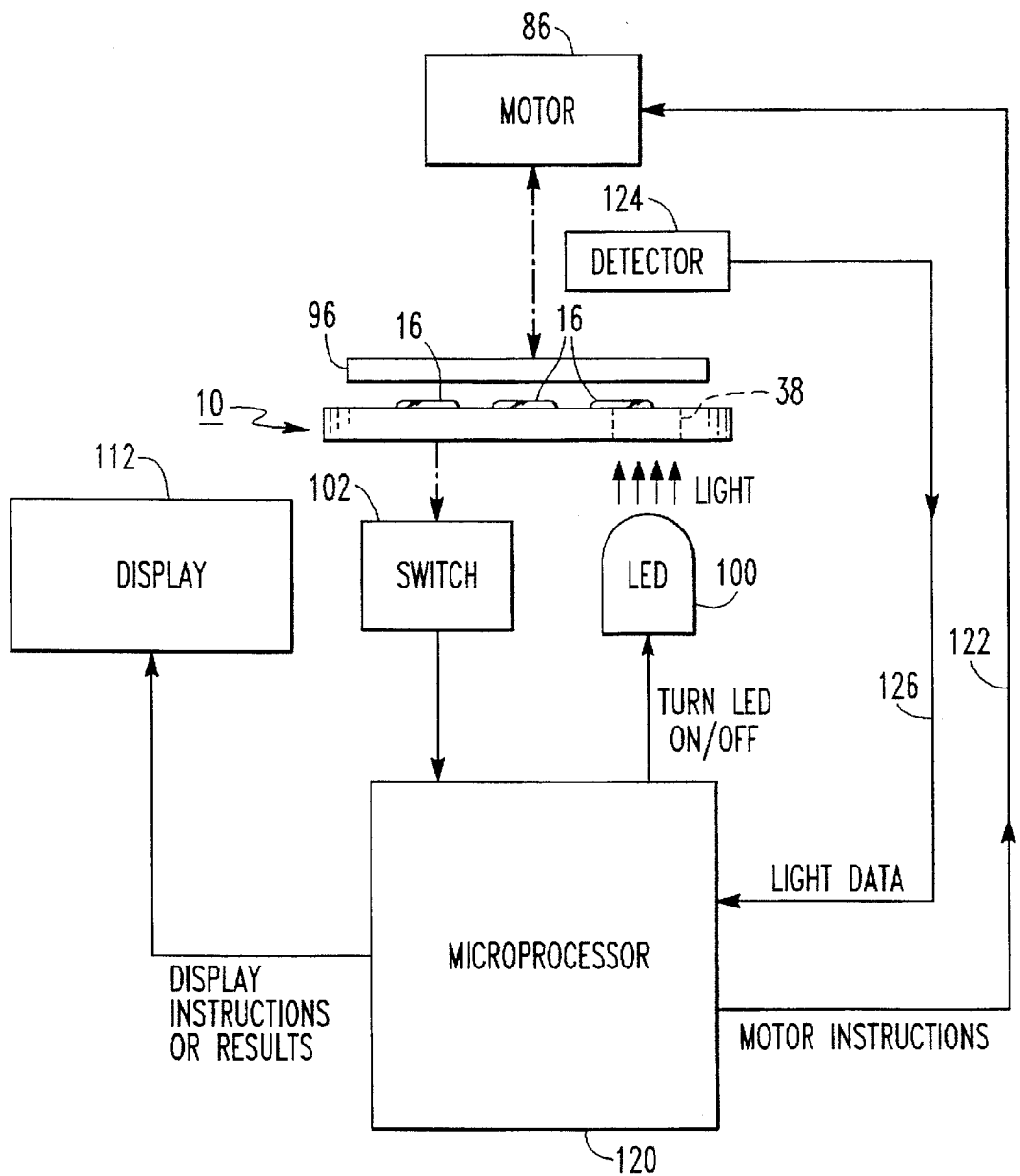
FIG. 12 is a block diagram of apparatus for practicing the present invention.

FIG. 12 is a block diagram illustrating certain components, including those previously described, cooperating to achieve improved mixing. The assay device 10, illustrated in an end view, when inserted in the unit 110 (FIG. 11), causes switch 102 to indicate to the microprocessor 120 that a card is in place whereupon microprocessor provides, on line 122, a signal to motor 86 to cause platen 96 to engage the reservoirs 16 so as to discharge the reagents therein at a high velocity for initial mixing. At this point the LED 100 may also be turned on by the microprocessor 120, with the light passing through optical viewing area 38 and being received by detector 124 the output signal or signals from which are provided to microprocessor 120 via line 126.

Figure 13A:
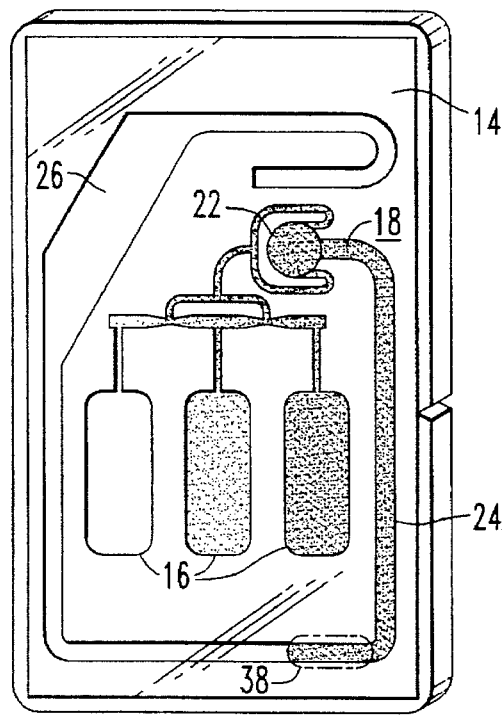
FIG. 13A–13D illustrate fluid flow in the assay device during operation of the apparatus of FIG. 12.

With additional reference to FIGS. 13A to 13D, which shows the housing 14 in rudimentary form, FIG. 13A illustrates the situation where high speed activation has taken place and fluid in the downstream portion of track 18 has arrived at optical window 38. The arrival of the fluid at the optical window 38 blocks the LED light to some extent resulting in an output from the detector 124 indicative of such fact. If desired, the microprocessor may have a timeout such that if fluid has not reached the optical viewing area 38 after a predetermined time after an activation of motor 86, the test may be aborted by a suitable message on display 112.

Figure 13B:
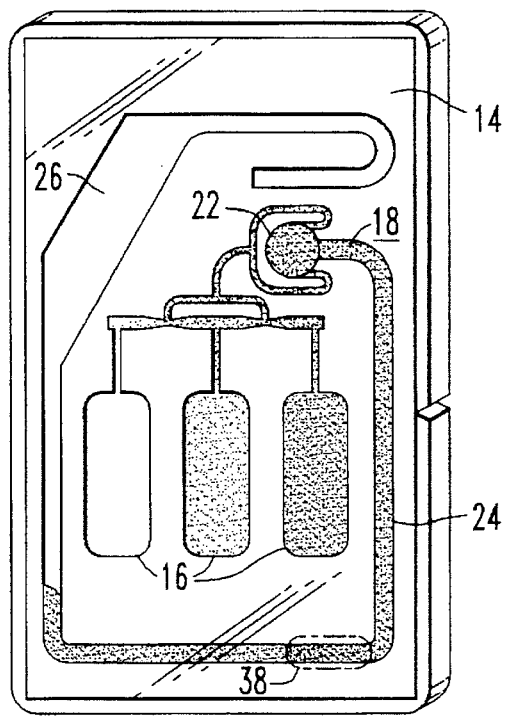
Figure 13C:
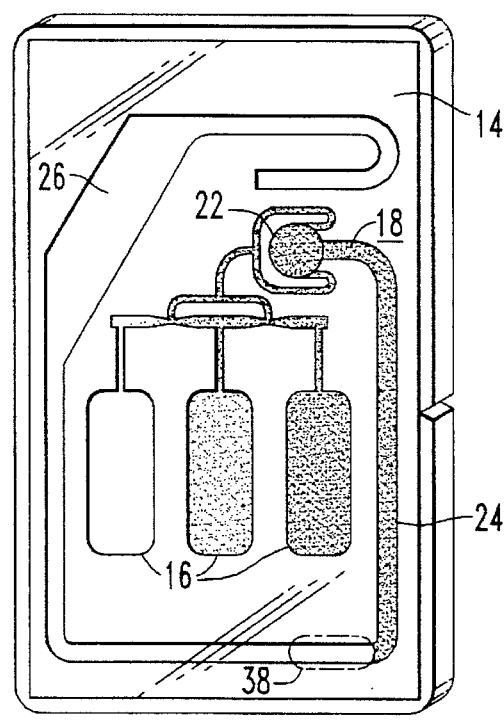
Figure 13D:
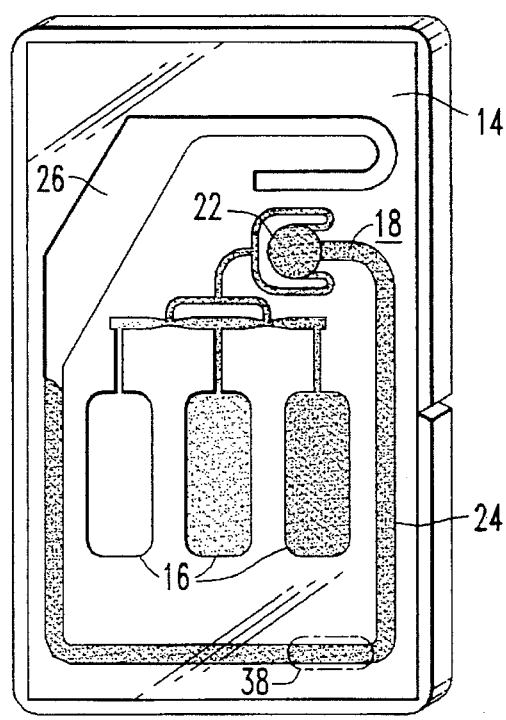
Figure 14:
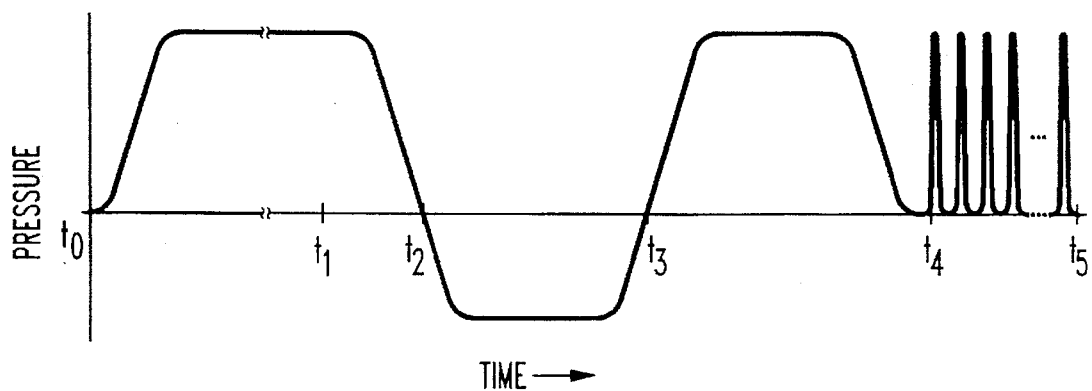
FIG. 14 is an idealized curve of pressure vs. time, illustrating the present invention.

In accordance with one aspect of the invention, if the fluid has reach optical viewing area 38 within the prescribed time, it is allowed to progress past the optical viewing area 38 for a second predetermined period of time, as indicated in FIG. 13B. After this second period of time, the microprocessor instructs the motor to operate at a high speed reverse to reverse the applied pressure on the reservoirs 16 thereby drawing the mixed fluid back through the track 24 to a position, for example, as illustrated in FIG. 13C. The motor is then run in a forward direction a second time past the optical window 38 to a position such as illustrated in FIG. 13D. The motor is then run at a slower speed until enough time has passed for a reaction to start such that an analysis may take place.

FIG. 14 illustrates a pressure vs. time curve which describes the improved mixing operation. At time $t_o$, the card is inserted and the motor causes a high pressure to be applied to reservoirs 16 for discharge of the reagents. At a first period of time $t_1$, the fluid should have reached optical viewing area 38 and if not, the test is aborted. If it has reached the area 38, then the high pressure is continued and thereafter reduced, such that at time $t_2$ the pressure is reversed for a time period $t_2$ to $t_3$. At $t_3$ the pressure is again increased for high speed operation and thereafter, at time $t_4$, a pulsing operation from $t_4$ to $t_5$ will take place resulting in a second and slower fluid velocity. Although FIG. 14 illustrates one pressure reversal, it is understood that a plurality of such reversals may take place prior to the slow speed operation.

Track 18 at the point of the viewing area 38 has a thickness which facilitates the use of small quantities of reagents, does not interfere with the agglutination process and is insufficient to substantially interfere with the passage of light through an aqueous reaction system contained therein. The thickness may be determined empirically and should simply be insufficient to interfere with the optical procedures. Moreover, since the reaction involves agglutination, track 18 must have sufficient thickness so that it does not mechanically interfere with the development and movement of the agglutinate.

The device 10 may have great utility for detection of controlled drugs or materials such as explosives. In particular the device may be utilized to analyze for the presence of cocaine. A reaction environment is prepared in which the rate of an agglutination reaction is related in a smooth fashion to concentration over some useful range of a target analyte. A light source and photodetector monitor the reaction and measure the intensity of the light signal.

Although the device 10 and system is based on the measurement of transmission through the track 18, it is also contemplated that light reflectance from the track 18 might also be measured as an indicator of the extent of agglutination.

While there has been illustrated and described what are at present considered to be a preferred embodiment of the present invention, it will be understood by those skilled in the art that various changes and modifications may be made, and equivalents may be substituted for elements thereof without departing from the true scope of the invention.

In addition, many modifications may be made to adapt a particular element, technique or implementation to the teaching of the present invention without departing from the central scope of the invention. Therefore, it is intended that this invention not be limited to the particular embodiments disclosed herein, but that the invention include all embodiments falling within the scope of the appended claims.

We claim:

1. Apparatus for use in determining the presence of a target analyte in an unknown sample, comprising:
    a) an assay card including i) an entry port for receiving said sample, ii) a plurality of reservoirs each containing a reagent for detection of the target analyte and being of the type which reduces in volume when positive pressure is applied to expel the contents thereof and will return toward its original volume when said applied pressure is reversed, iii) a fluid conveying track fluidly connecting said reservoirs with said entry port and extending downstream thereof, and iv) a viewing area positioned for viewing and analyzing the fluid contents of a downstream portion of said track;
    b) actuator means for applying pressure to said reservoirs to expel the contents thereof into said track to mix them together and with said sample in said entry port;
    c) detector means operable to provide an output signal indicative of the presence of the mixed reagents at said viewing area; and
    d) control means operable in response to said output signal to cause said actuator means to reverse the applied pressure at least once, to reverse the direction of fluid flow in said track and to thereafter again apply positive pressure, whereby the reversal of fluid flow further agitates and mixes said reagents and sample.

2. Apparatus according to claim 1 wherein:
    said control means is operable to cause said actuator means to reverse the applied pressure only after a predetermined period of time has elapsed after the provision of said detector output signal.

3. Apparatus according to claim 2 wherein:

said predetermined period of time is less than one-half second.

4. Apparatus according to claim 1 which includes:

a light source positioned on one side of said card and operable to project light through said viewing area;

said detector being positioned on an opposite side of said card to intercept said light projected through said viewing area; and wherein said output signal is caused by a drop in light intensity at said viewing area when said fluid passes by.

5. Apparatus according to claim 1 wherein:

said reservoirs are formed from a resilient film.

6. Apparatus according to claim 1 wherein:

said control means is operable to cause said actuator means to reduce the pressure applied to said reservoirs after the last reversal of fluid flow.

* * * * *